United States Patent [19]

Gaba

[11] Patent Number: 5,058,764

[45] Date of Patent: Oct. 22, 1991

[54] MOUNTING BRACKET HAVING A HIDDEN LOCK FOR A SHARPS COLLECTION SYSTEM

[75] Inventor: Rodolfo Gaba, Simi Valley, Calif.

[73] Assignee: Devon Industries, Inc., Chatsworth, Calif.

[21] Appl. No.: 638,362

[22] Filed: Jan. 4, 1991

[51] Int. Cl.$^5$ ............................................. F16N 13/00
[52] U.S. Cl. .................................. 220/481; 220/908; 248/154; 248/313; 248/907
[58] Field of Search ..................... 220/481, 85 H, 908; 248/907, 154, 313

[56] References Cited

U.S. PATENT DOCUMENTS

| | | | |
|---|---|---|---|
| 2,450,722 | 10/1948 | Drije | 220/481 X |
| 2,606,732 | 8/1952 | Luomala | 248/313 X |
| 2,846,173 | 8/1958 | Grovesteen | 248/313 X |
| 3,075,692 | 1/1963 | Lumley | 220/481 X |
| 3,104,860 | 9/1963 | Brittain | 248/313 X |
| 3,240,459 | 3/1966 | Spohn, Jr. | 248/907 X |
| 3,367,528 | 2/1968 | Cowan et al. | 220/481 X |
| 3,568,966 | 3/1971 | Lucci | 248/154 |
| 4,071,976 | 2/1978 | Chernewski | 248/313 X |
| 4,828,107 | 5/1989 | Spencer | 220/908 X |

Primary Examiner—Steven M. Pollard
Attorney, Agent, or Firm—Poms, Smith, Lande & Rose

[57] ABSTRACT

A mounting bracket for a container, such as a container for hospital sharps, is shown. The container includes a flanged top with front, side, and rear walls, extending from the flanged top to a bottom enclosure surface. At the juncture between the rear wall and bottom surface is a container recess having a closed aperture extending upwardly from the top wall of the recess. A mounting bracket includes an upper flange and a lower housing adapted to be received within the container recess for supporting the container. The upper flange of the container is engaged by the upper flange of the mounting bracket through a slot and flange combination. The lower housing of the mounting bracket includes a latching bar which is spring loaded for urging the latching bar into the closed aperture within the container recess. The container and mounting bracket are dimensioned so that the container completely covers and hides the mounting bracket, while the housing on the lower surface of the mounting bracket fits within the container recess for hiding the housing and for locking the container to the bracket.

9 Claims, 3 Drawing Sheets

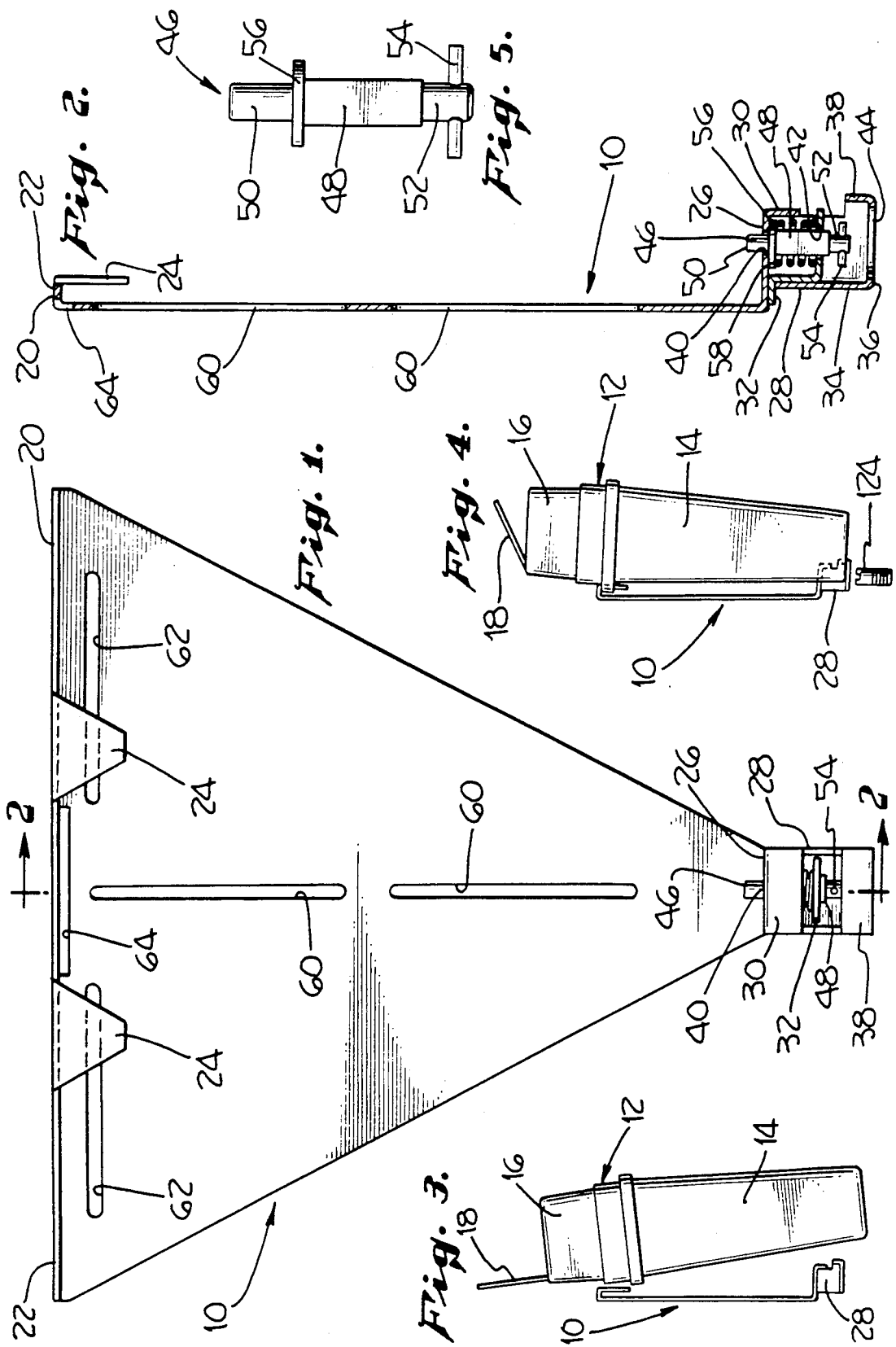

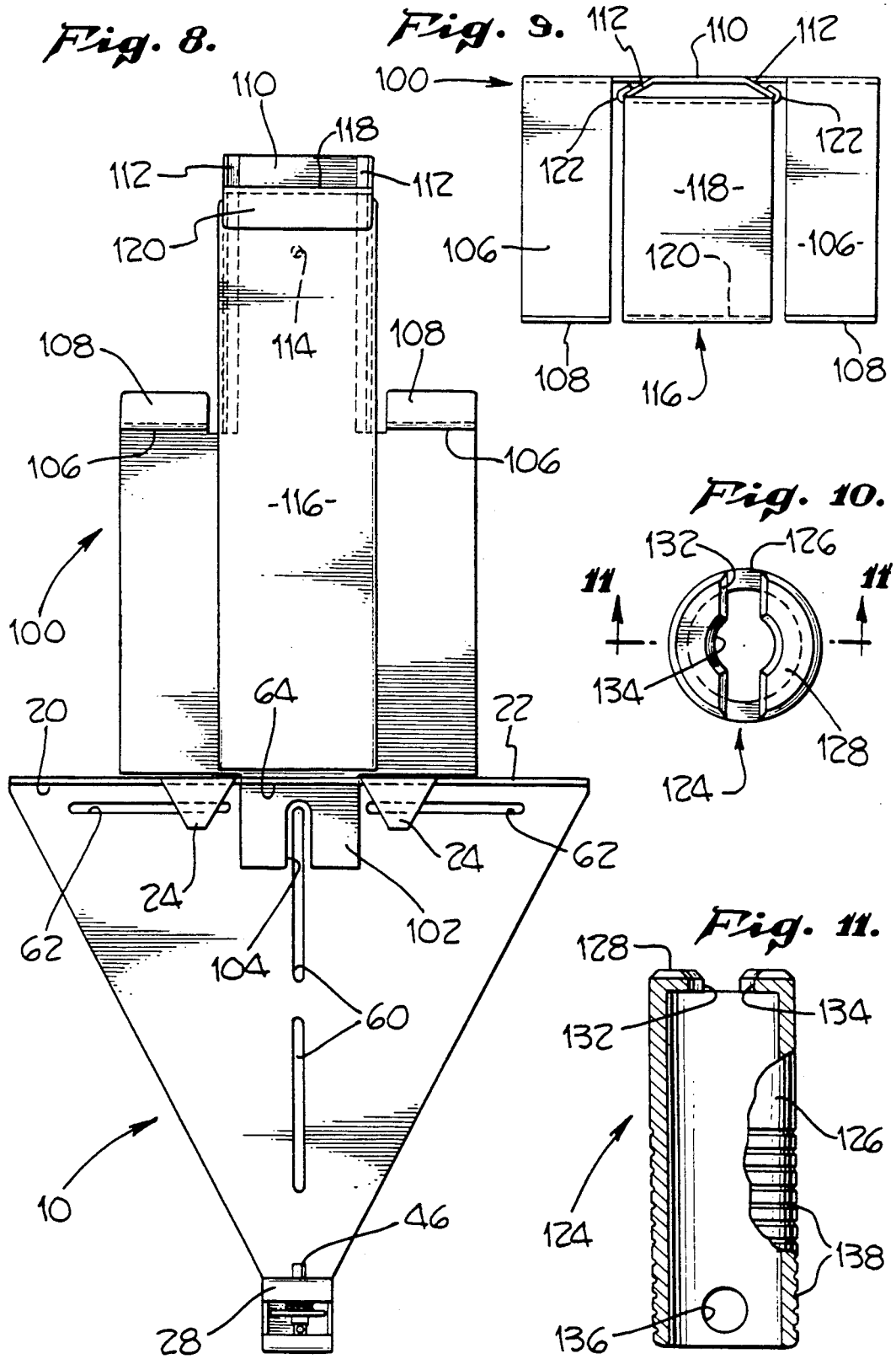

MOUNTING BRACKET HAVING A HIDDEN LOCK FOR A SHARPS COLLECTION SYSTEM

BACKGROUND OF THE INVENTION

1. Field of the Invention

The present invention relates to a mounting bracket for a container and, more particularly, to a mounting bracket having a hidden lock for mounting a sharps collection and disposal system that may be used, for example, in a patient's hospital room.

2. Brief Description of the Prior Art

Various types of containers for hospital use have been developed for receiving medical waste in a surgical operating room, pre-op or post-op room, or a patient's room. These containers are particularly designed to protect the user of such containers, such as doctors, nurses, or other hospital personnel, from the hospital waste products that may be disposed therein. Such hospital waste products might include surgical sharps, such as needles, syringes, scalpel blades, or the like, or might include gauzes, bandages, or sponges. It is important to prevent the user of a sharps container from being accidentally cut or punctured by its contents. An example of one such container which prevents contamination is shown in a co-pending patent application entitled "Tortuous Path In-Patient Room Medical Waste Disposal Container," filed on Oct. 4, 1990, as Ser. No. 07/595,748, which is assigned to the same assignee as the present invention.

Examples of other disposable containers for use in surgical room environments, including: Pat. No. 4,494,652, entitled "Container for Sharps;" Pat. No. 4,552,280, entitled "Container for Waste Products;" Pat. No. 4,453,648, entitled "Disposal Bin;" and Pat. No. 5,580,688, entitled "Container Having Plural Closures."

In addition to protecting the user of a sharps container from its contents and to being easily sealed and disposed of, a sharps collection and disposal system should be readily available within a patient's room, an operating room, or a pre-op or post-op room. This readily available feature can be accomplished by providing a mounting bracket for mounting the sharps collection system at a convenient location near an operating area, or a bed location in a pre-op, post-op, or patient's room.

Thus, one object of the present invention is to provide a mounting bracket into which a sharps collection system may be easily inserted and permanently attached.

Another object of the present invention is to provide a mounting bracket from which the sharps collection system may be easily detached and removed.

It is a further object of the invention to provide a mounting bracket which locks the sharps collection system against spillage or tampering.

A still further object is to provide a mounting bracket which is easily and economically fabricated, hidden from the view of its user or patient, and which hides its locking arrangement so that a user, patient or visitor to the hospital site where the mounting bracket is used could not easily tamper with it.

SUMMARY OF THE INVENTION

In accomplishing the foregoing objects and other objects, there is provided a container for hospital sharps and other waste having an upper flange, front, side and rear walls extending from the upper flange and a bottom closure surface. Also provided is a top for the container which does not form a part of the present invention. The rear wall and bottom surface of the container include a container recess with a closed aperture therein. A mounting bracket which may be wall mounted is arranged with an upper flange that engages the upper flange of the container and with a lower housing that is received by the container recess for supporting the container. The lower housing includes a latching bar which is urged by a spring into engagement with the closed aperture found within the container recess.

The sharps container is mounted by tilting the container to insert flanges on either the mounting bracket or container into slots on either the container or mounting bracket. Once the flanges are engaged within the slots, the lower portion of the container is rotated about the engaged flanges and slots until the lower housing on the mounting bracket engages the container recess. At this point, the spring-loaded latching bar is displaced for latching engagement into the closed aperture within the container recess.

The latching bar is provided with a hook which may be engaged by a key. The sharps container is removed from its mounting bracket by inserting the key into the lower housing so that an aperture in the key engages the latch bar hook. The key is then rotated approximately 90° and pulled to disengage the spring-loaded latch bar from the closed aperture within the container recess to permit the removal of the container.

BRIEF DESCRIPTION OF THE DRAWINGS

Further advantages and objects of the present invention will be understood after careful consideration of the following specification and drawings, wherein:

FIG. 1 is a front view of the mounting bracket;

FIG. 2 is a cross-sectional view taken along line 2—2 of FIG. 1;

FIG. 3 is a side view showing a sharps collection system being inserted into the mounting bracket;

FIG. 4 is a side view similar to FIG. 3 showing the sharps collection system prior to removal from the mounting bracket;

FIG. 5 is a detailed, front view of the latching bar;

FIG. 8 is a front view of the mounting bracket shown in FIG. 1 with a second and third mounting bracket attached thereto;

FIG. 9 is a top view of the second and third mounting bracket shown in FIG. 8;

FIG. 10 is a top view of a key used to unlock the sharps container from its mounting bracket; and FIG. 11 is a cross-sectional view taken along line 11—11 of FIG. 10.

DESCRIPTION OF THE PREFERRED EMBODIMENTS

Figure 6:
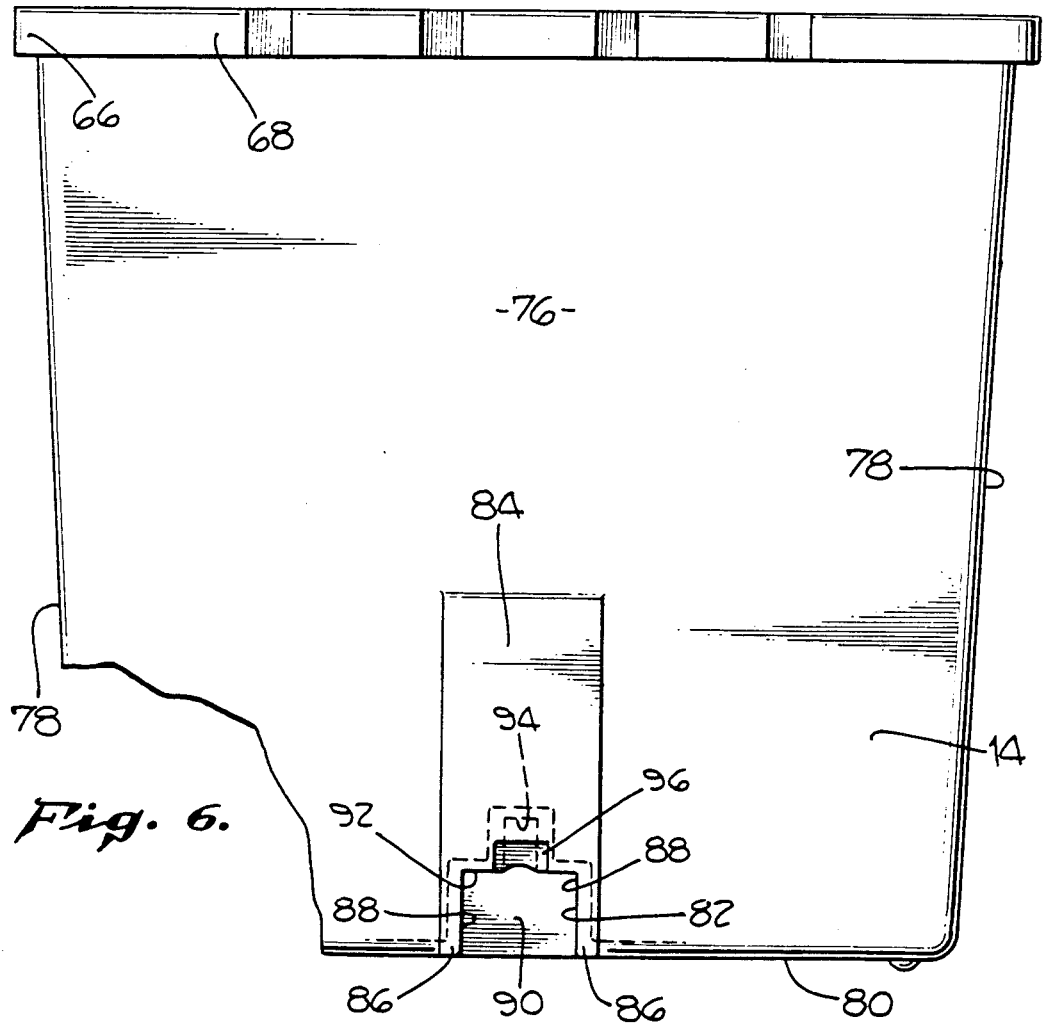
FIG. 6 is a rear view of the sharps collection container.

Referring now to the drawings, a mounting bracket 10 for use in the present invention is best seen in FIGS. 1 and 2. This mounting bracket 10 works in conjunction with a sharps collection and disposal system 12 which includes a sharps collection container 14 and a collection top 16 having a tortuous entry path. See FIGS. 4 and 5. The collection top 16 is closed by a cover 18 which may be snapped into a locked position by suitable latching fingers and slots, best seen in co-pending patent application Ser. No. 07/595,748, filed Oct. 4, 1990, which is incorporated herein by reference.

As seen in FIGS. 1 and 2, mounting bracket 10 includes an upper portion 20 formed by a flange 22 bent at right angles to the plane of the bracket. In the preferred embodiment, flange 22 has a pair of extended flanges 24 bent at right angles to flange 22 and, thus, parallel to the plane of flange 10. The extended flanges 24 are triangularly shaped with a truncated lower end to permit the flanges to readily fit within a slot in the sharps collection container 14 to be described below. In the preferred embodiment, the extended flanges 24 are formed on the upper flange 22 of the mounting bracket 10. In an alternative embodiment, the upper flange 22 could be fitted with slots while the sharps collection container 14 could be fitted with extended flanges.

In the preferred embodiment, the plane surface of the mounting bracket 10 is formed as a triangle with its lower portion bent at right angles to form an upper surface 26 of a latch housing 28. Latch housing 28 may be seen in cross section in FIG. 2, wherein the upper surface 26, first bent to parallel upper flange 22, is then bent at right angles to form a front closure surface 30. A Z-shaped bracket 32 is then placed against the lower surface of upper housing flange 26 and attached thereto, as by spot welding. The lower portion of the Z-shaped bracket 32 extends parallel to upper housing surface 26 and terminates in line with and just below the front closure surface 30. Lastly, a four-sided, lower housing closure 34 is placed against the vertical surface of the Z-shaped bracket 32 and attached thereto, as by spot welding. It will be seen in FIGS. 1 and 2 that the four-sided housing 34 is formed from a piece of sheet metal bent with three vertical sides which form a general U-shape to enclose the latching housing 28. The lower surface of the middle vertical side of the U-shaped enclosure extends and is bent to form a lower housing closure wall 36 whose forward-most end is then upwardly bent to form a second front closure 38 which is parallel to the first-mentioned front closure 30 and which completes the partial closure of the front surface of latch housing 28.

As seen from FIG. 2, upper housing surface 26 is provided with a circular aperture 40 while the lower surface of the Z-shaped bracket 32 is provided with a square aperture 42. Lastly, the lower housing surface 36 is provided with a much larger circular aperture 44. Slidably inserted within apertures 40 and 42 is a latch bar 46, shown in detail in FIG. 5. The latch bar 46 is, in the preferred embodiment, formed from a square piece of bar stock so that its center section 48 has a square cross-section which rides within the square aperture 42. An upper section 50 of the latch bar 46 is turned on a lathe, for example, to form a circular cross-section having a rounded end. The lower section 52 of latch bar 46 is also turned on a lathe, for example, to form a rounded cross section. The lower section 52 is then provided with an aperture, as by drilling, to receive a pin 54, such as a roll pin, which forms a hook for the latch bar 46. The assembly of the latch bar within housing 28 is completed by press fitting, for example, a washer 56 over the circular cross section of upper section 50. A helically wound compression spring 58 is then inserted between washer 56 and the lower surface of the Z-shaped bracket 32 to urge the latch bar 46 in an upward direction as seen in FIG. 2.

The mounting bracket 10 is provided with a plurality of vertical slots 60 and horizontal slots 62, FIG. 1, through which suitable mounting screws may be inserted for attaching the mounting bracket 10 to a wall within the room of a hospital patient, an operating room, or a pre-op or post-op room. Finally, a slot 64 for mounting a second bracket, to be described below, is provided at the bend between the plane of mounting bracket 10 and the upper flange 22.

Figure 7:
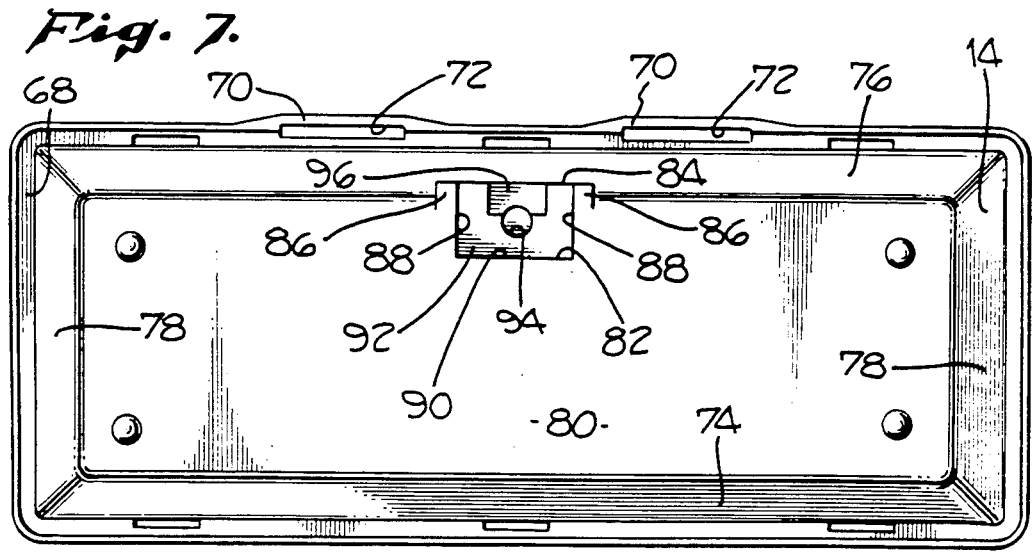
FIG. 7 is a bottom view of the sharps collection container.

Referring now to FIGS. 6 and 7, the sharps collection container 14 is shown without the collection top 16 having the tortuous entry path. The container 14 includes an upper portion 66 formed by a flange 68. Flange 68 includes two expanded sections which form small extended platforms 70 into which slots 72 may be formed as, for example, the container 14 is molded through a suitable molding process. Extending below the flange 68 are front and rear surfaces, 74 and 76, and side surfaces 78, all of which terminate in a bottom surface 80.

The rear wall 76 and bottom surface 80 include a container recess 82 formed in a more vertical, rear wall portion 84 which permits the start of recess 82 at a point slightly outside the intersection of rear wall 76 and bottom surface 80. The recess 82 is formed in wall portion 84 between a pair of extensions 86 which establish the side walls 88 of the recess 82 and which extend into container 14 to terminate at a back recess wall 90. The upper edges of the side walls 88 and back wall 90 terminate at a top wall 92 to complete the recess. A closed aperture 94 is molded into the top wall 92 to receive the latching bar 46. Recess 94 is closed to prevent leakage from the sharps container 14. A sloping surface 96 is molded into the wall portion 84 and top wall 92 and leads into the closed aperture 94 to engage the rounded upper section 50 of latch bar 46 and to urge the latch bar 46 in a downward direction before the latch bar 46 passes into aperture 94. This permits the easy assembly and locking of the container 14 into the mounting bracket 10, as seen in FIGS. 3 and 4.

In one embodiment, a second container may be mounted above mounting bracket 10, as shown in FIGS. 8 and 9. The mounting bracket 10 is provided with the slot 64 to receive a second bracket 100, best seen in FIG. 8. The second bracket 100 is generally planar, having a lower and downwardly extending tab 102, which passes through slot 64 and which, in turn, has a slot 104 therein to provide a clearance for vertical slot 60 within the mounting bracket 10. Extending from the bracket 100, above the lower tab 102, are a pair of container support arms 106 which are bent at 90° to the plane of the second bracket 100 and from whose outermost end a pair of upwardly extending tabs 108 are bent at a second 90° angle to parallel the plane of the second bracket. Between arms 106, the remaining portion of the second bracket 100 forms an upwardly extending track 110 whose outer edges have been bent at less than 90° to form a pair of track flanges 112. An aperture 114 completes the second bracket 100 and is used to receive a screw, for example, for fastening the bracket 100 to the wall above the mounting bracket 10. The tab 102 inserted into slot 64 of bracket 10 completes the mounting of the second bracket 100.

The container support arms 106 are complemented by a third bracket 116 having a container retaining arm 118 extending at right angles to the plane of the third bracket 116 and a tab 120 downwardly bent at 90° to the arm. The third bracket 116 includes a pair of flanges 122, best seen in FIG. 9, which are bent at more than 90° to fit about the track flanges 112 and to retain the third bracket in a sliding relationship upon the track 110 of the second bracket 100. It will now be seen in FIG. 8 that the weight of the third bracket causes the bracket to slide with the third bracket flanges 122 sliding over the track flanges 112. It will also be seen that a second container, such as a glove box holder, may be placed upon the support arms 106, while the retaining arm 118 rests upon the upper surface of the second container, not shown.

A key 124, seen in FIGS. 10 and 11, is provided for use with the pin or hook 54 and its related latch bar 46. The key 24 consists of a tubular member 126 whose upper end is closed by an end wall 128. The end wall is relieved with a slot 132 having opposing semi-circular cut-outs 134. The upper edges of the slot and cut-outs, 132 and 134, have been chamfered to provide for the easy alignment and clearance of the circular lower section 52 and pin 54 of latch bar 46. An aperture 136 is provided in the tubular side walls of key 124 which is aligned with the slot 132 to permit the user to easily orient the slot 132 With pin 54. Optionally, the outer surfaces of tubular member 126 may be knurled or provided with a series of parallel grooves 138 to make the key 124 easier to handle.

In operation, the sharps container 14 of the sharps collection and disposal system 12 is aligned with brackets 10 so that the extended flanges 24 of bracket 10 are inserted into slots 72 in the flange 68 of container 14. Container 14 is then rotated about the flanges 24 and slots 72 until the sloping surface 96 of container recess 82 engages the latch bar 46. As continual rotation occurs, the latch bar 46 is urged downwardly by sloping surface 96 against spring 58 until the rounded, upper section 50 of bar 46 reaches its unlocked position and slips into the closed aperture 94 of container recess 82 for latching the container 14 against bracket 10. In its latched position, as shown in FIG. 4, the sharps collection container 14 is supported by the engagement of surface 92 from the container recess 82 against the upper housing surface 26 of latch housing 28. The sharps collection and disposal system 12 may then be used to collect infectious wastes, such as needles, syringes, scalpel blades, bandages, or the like.

When it is desired to remove the sharps collection and disposable system 12, either because it is filled or a patient has left the room in which it is mounted, removal is accomplished by first closing the cover 18 on top 16 so that the cover snaps securely into its shut position. The key 124 is then oriented so that its slot 132 is aligned perpendicularly with the planar surface of bracket 10 where the key may be then inserted through the circular aperture 44 in the lower housing closure 36. Key orientation is accomplished by the user feeling the position of aperture 136 in the tubular wall 126 of key 124 which is parallel with hook slot 132. The pin or latch hook 54 is oriented by the square aperture 42 in which the square cross-section of the center section 48 of latch bar 46 slides to be perpendicular to the plane of mounting bracket 10. The slot 132 and semi-circular cut-outs 134 of key 124 then pass over the pin 54 and circular, lower portion 52 of latch bar 46. The key 124 is then rotated approximately 90° and pulled in a downward direction to place latch bar 46 in its unlatched position to disengage the upper section 50 of latch bar 46 from the closed aperture 94 in the retainer recess 82. This permits the easy removal of the container 14 and its sharps collection system 12.

In addition to the embodiments described hereinabove, those skilled in the art will recognize that other embodiments are possible within the teachings of the invention. Accordingly, the present invention should be limited only by the appended claims.

What is claimed is:

1. A mounting bracket for a container, comprising:
   a wall mounting bracket having an upper portion and a lower portion;
   a pair of extended flanges located on the upper portion of said mounting bracket;
   a housing located on the lower portion of said housing bracket;
   said housing mounting a latch bar and a spring for urging said latch bar into an extended position;
   a container having an upper and a lower portion;
   a pair of slots for receiving said pair of extended flanges located in the upper portion of said container;
   a recess for receiving said housing located in the lower portion of said container;
   said recess having an aperture therein for receiving said latch bar, wherein said bracket housing receives said container recess to support said container and said latch bar prevents the removal of said container from said bracket.

2. The mounting bracket of claim 1, additionally comprising:
   said container recess having a sloping surface leading to said aperture to urge said latching bar into an unlatched position to permit said latching bar to be received into said aperture.

3. The mounting bracket of claim 1, additionally comprising:
   said latching bar having a hook;
   said housing having an aperture therein to permit access to said latch bar hook; and
   a key having an aperture therein for receiving said latching bar hook, said key adapted to pass through said housing aperture to receive said latch bar hook and to urge said latch bar into an unlatched position by removing said latch bar from its extended position in said recess aperture for unlatching said container from said bracket.

4. The mounting bracket of claim 1, additionally comprising:
   said latch bar including means to orient said latch bar hook in a constant orientation; and
   said key including means to orient said key in a constant orientation.

5. The mounting bracket of claim 1, additionally comprising:
   said mounting bracket having a slot therein;
   a second bracket having a planar, downwardly extending tab for insertion into said slot, a pair of extending arms which extend at right angles to the plane of said second bracket for supporting a second container, and an upwardly extending tab having a pair of flanges which extend at less than a right angle to the plane of said second bracket; and
   a third bracket having a pair of flanges which extend at more than a right angle to the plane of said third bracket to enclose said pair of flanges on said upwardly extending tab for sliding engagement therewith, said third bracket further having an extending arm which extends at a right angle to the plane of said third bracket for resting upon said second container.

6. A hidden and locked mounting bracket for a container, comprising:
   a container having an upper flange, front, side, and rear walls extending from said flange, and a bottom closing said walls;
   said container having a container recess in said rear wall and said bottom with a closed aperture therein;
   a mounting bracket having an upper flange and a lower housing adapted to be received in said container recess;
   said upper flange of said container and said upper flange of said bracket including slot and flange means for engagement therebetween;
   said lower housing including a latch bar and a spring for urging said latch bar into an extended position for engaging said closed aperture in said container recess, wherein said latch bar locks said container into said slot and flange means and said container hides said mounting bracket behind said rear wall with said lower housing hidden in said container recess.

7. The mounting bracket of claim 6, additionally comprising:
   said slot means including a slot in said upper flange of said container; and
   said flange means including a flange extending from said upper flange of said mounting bracket.

8. The mounting bracket of claim 6, additionally comprising:
   said slot means including a slot in said upper flange of said mounting bracket; and
   said flange means including a flange extending from said upper flange of said container.

9. The mounting bracket of claim 6, additionally comprising:
   said latch bar having a hook;
   said housing having an aperture therein to permit access to said latch bar hook; and
   a key adapted for insertion through said housing aperture and engagement with said latch bar hook.

* * * * *